United States Patent [19]

Brandenburger et al.

[11] Patent Number: 5,406,950
[45] Date of Patent: Apr. 18, 1995

[54] INHALABLE CONTRAST AGENT

[75] Inventors: Gary H. Brandenburger, Florissant; Gary L. Cantrell, Troy, both of Mo.

[73] Assignee: Mallinckrodt Medical, Inc., St. Louis, Mo.

[21] Appl. No.: 172,100

[22] Filed: Dec. 23, 1993

[51] Int. Cl.$^6$ .................................................. A61B 8/00
[52] U.S. Cl. ................................. 128/662.02; 128/654
[58] Field of Search ............... 128/662.02, 654; 424/9, 424/44, 450, 43; 436/829

[56] References Cited

U.S. PATENT DOCUMENTS

| | | | |
|---|---|---|---|
| 4,718,433 | 1/1988 | Feinstein | 128/662.02 |
| 5,088,499 | 2/1992 | Unger | 128/662.02 |

FOREIGN PATENT DOCUMENTS

| | | |
|---|---|---|
| 9004943 | 5/1990 | WIPO . |
| 9305819 | 4/1993 | WIPO . |
| 9306869 | 4/1993 | WIPO . |

OTHER PUBLICATIONS

Lee, Shih-Wei et al., "Development of an Aerosol Dosage Form Containing Insulin", *J. Pharmac. Sci.*, vol. 65, No. 4, Apr. 1976, pp. 567–572.

Berthezene, Yves, et al., "Contrast–enhanced MR Imaging of the Lung: Assessments of Ventilation and Perfusion", *Radiology*, vol. 183, No. 3, Jun. 1992, pp. 667–672.

Yoshida, H. et al., "Absorption of Insulin Delivered to Rabbit Trachea Using Aerosol Dosage Form", *J. Pharmac. Sci.*, vol. 68, No. 5, May 1979, pp. 670–671.

*Primary Examiner*—George Manuel
*Attorney, Agent, or Firm*—Rothwell, Figg, Ernst & Kurz

[57] ABSTRACT

A contrast agent is administered to a patient by inhalation into the patient's lungs. The agent is transmitted through the lungs into the patient's bloodstream, for transport to a non-lung portion of the patient to be imaged. A portion of the patient containing the microbubbles is subjected to an ultrasound scan, so as to obtain an enhanced ultrasonically generated image of the patient.

38 Claims, No Drawings

INHALABLE CONTRAST AGENT

BACKGROUND OF THE INVENTION

1. Field of the Invention

The present invention relates to the field of imaging internal portions of animal bodies.

2. Description of the Background Art

Images of internal structures and organs within a patient can be utilized for performing diagnosis and monitoring of patients. Such internal images can be obtained, for example, by ultrasonic imaging, magnetic resonance imaging (MRI) and optical imaging.

Ultrasonic images are formed utilizing reflected ultrasound waves, which are detected and electronically converted into a visual display.

Ultrasonic imaging is particularly desirable when the internal structures of interest within the patient can be imaged utilizing the reflected ultrasound alone. However, it sometimes is necessary to enhance the contrast of an ultrasound image by introducing a contrast agent into the patient. Heretofore, such ultrasound contrast agents typically have been introduced into patients by injection. Unfortunately, injection of an ultrasound contrast agent into a patient destroys the otherwise non-invasive advantage of ultrasonic imaging.

Other types of internal imaging, such as MRI and optical imaging, often also require injection of contrast agents to enhance the images.

PCT International Publication No. WO 93/06869 to Vanderripe proposed inhalation of various gases to produce supersaturation in the blood for ultrasound contrast.

Contrast enhanced magnetic resonance imaging of the airways of the lungs has been proposed using aerosolized gadopentetate dimeglumine in *Radiology*, 183: 667–672 (1992). However, there is no suggestion of delivery of contrast agent into the pulmonary circuit for MRI enhancement of non-lung tissue.

There remains a need in the art for methods and compositions for enhancing contrast during internal imaging of non-lung tissue in patients, without the need for invasively injecting a contrast agent into the patient.

SUMMARY OF THE INVENTION

In accordance with the present invention, a method of imaging a non-lung portion of a mammal comprises administering an aerosol contrast agent comprised of particles to a mammal by inhalation of the agent into a lung of the mammal. The contrast agent is transmitted through the lung into the mammal's bloodstream, and transported by the bloodstream to the portion of the mammal to be imaged. The mammal then is subjected to an imaging scan, so as to obtain an enhanced image of the non-lung internal portion of the mammal.

The invention further encompasses an inhalable contrast agent which comprises an aerosol including particles which are capable of entering a mammal's bloodstream through inhalation of the aerosol into a lung of the mammal. The particles form a contrast medium in the bloodstream which is capable of enhancing images of the mammal.

DETAILED DESCRIPTION OF THE PREFERRED EMBODIMENTS

The contrast agents of the present invention do not require invasive injection of the agents into the body for internal image enhancement. Instead, the aerosol contrast agents of the present invention are administered to a mammal by inhalation into a lung or lungs of the mammal. The transport of such an agent is facilitated by the lung's large surface area (50 to 100 $m^2$), thin membrane thickness (about 0.2 m), high blood flow and rapid absorption characteristics.

Examples of inventive contrast agents include ultrasound contrast agents, MRI contrast agents and optical contrast agents. The inhaled contrast agents of the invention also can provide therapeutic treatment of the patient, if suitably configured.

An ultrasound contrast agent in accordance with one embodiment of the present invention comprises an aerosol including particles which are capable of entering the mammal's bloodstream after inhalation of the aerosol into the mammal's lungs. The particles of the aerosol can be, for example, liquid or solid. The term "solid" as used herein, is intended to mean all particles which are not liquid, including semi-solid particles.

The aerosol can be produced in any well known means, e.g., by suspending particles in suitable propellants, such as fluorocarbon propellants, hydrocarbon propellants, ether propellants or compressed gases. Such propellants can also be utilized to form microbubbles in ultrasound contrast agents according to the present invention. Where liquid particles are utilized, they can be saturated with one or more gaseous propellants.

Suitable fluorocarbon and fluorohalocarbon propellants may include chlorotrifluoromethane (Freon 11), dichlorodifluoromethane (Freon 12), dichlorotetrafluoroethane, difluoroethane, hexafluoroethane, hexafluoropropane, pentafluoropropane, octafluoropropane, decafluorobutane, trichlorotrifluoroethane, trifluoroethane, monochlorodifluoroethane, monochlorodifluoromethane, trifluoropropane and the like, including mixtures thereof.

Suitable hydrocarbon propellants in combination or individually may include n-butane, isobutane, propane, methylbutane, pentane, cyclopropane and the like.

Suitable ether propellants may include dimethyl ether, ethyl ether, ethyl methyl ether, methyl t-butyl ether, and the like, and mixtures thereof.

Suitable compressed gases which may be used as propellants and to form microbubbles may include carbon dioxide, nitrous oxide, nitrogen, helium, neon, argon, krypton, xenon, etc.

Alternatively, the aerosol can be produced utilizing a suitable atomizer or nebulizer.

Particles of the aerosol according to the invention generally are less than about 25 microns in size. In preferred embodiments, particles are small enough to penetrate deep into the lungs so that they readily cross the pulmonary alveolar membrane into the pulmonary bloodstream. Preferred particles are within a size range of about 0.1–10 microns in size, more preferably less than about 4 microns in size. In particularly preferred embodiments, the aerosol is made up of particles within the size range of about 0.1–3 microns so as to be transported into the alveolar sacs of the lungs.

According to one aspect of the invention for ultrasound use, inhaled particles are utilized as conveyors of gas precursors or microbubble progenitors. The inhalation of gas precursors or microbubble progenitors is far more efficient on a concentration basis than inhalation of a gas per se, as proposed in the previously cited Vanderripe PCT application.

In preferred embodiments, particles of the present invention for ultrasound use form microbubbles in the bloodstream of the mammal after entering the bloodstream through the mammal's lungs. The microbubbles formed in the bloodstream of the mammal are capable of enhancing an ultrasonically generated image of the mammal.

Suitable microbubbles must be sufficiently small so as not to cause embolism in the mammal in which they are formed.

Ultrasound image-enhancing microbubbles generally are less than about 15 microns in size, and preferably are predominantly about 8 microns in size or less. Microbubbles which are greater in size than about 8 microns generally are too large to pass through the capillary beds of the lungs. A discussion of the effect of microbubble size in injectable ultrasound contrast agents can be found in PCT International Publication No. WO 93/05819 to Steven C. Quay, claiming priority from U.S. Ser. Nos. 07/761,311 (filed Sep. 17, 1991) and 07/893,657 (filed Jun. 5, 1992), incorporated herein by reference.

In particularly preferred embodiments of the present invention, the microbubbles formed in the mammal's bloodstream are predominantly within the size range of about 0.5–8 microns, most preferably within the size range of about 1–7 microns.

In accordance with one aspect of the invention, the particles release ultrasound contrast-enhancing microbubbles upon entering the bloodstream of the mammal after inhalation. A particle comprised primarily of dilute (e.g., about 0.1–3% by weight) hydrogen peroxide ($H_2O_2$), or hydrogen peroxide progenitor, is an example. When given intravenously, Wang, et al. in *Chin. Med. J.* 1979; 92, 595–599; and in *Chin. Med. J.* 1979; 92, 693–702 and later Gaffney, et al. in *Am. J. Cardiol.* 1983, 52, 607–609 demonstrated the use of dilute hydrogen peroxide (0.1–3%, 0.5 to 2.0 mL) to produce oxygen gas microbubbles on contact with the oxidases and peroxidases of the blood to produce dense opacification of the right heart chamber with no complications. Particles of dilute hydrogen peroxide transported through the lungs into the pulmonary circulation likewise present ultrasonic opacification.

The hydrogen peroxide can also be provided as an adjunct to radiotherapy for treatment of neoplasms of the mammal.

In one preferred embodiment, the aerosol particles are liquid and the microbubbles formed in the bloodstream are comprised of a gas. Suitable microbubble gases for use in accordance with the present invention are disclosed in the previously cited PCT International Publication No. WO 93/05819, and include fluorocarbons such as decafluorobutane and perfluoropentane. Organic liquids which may be suitable for use in the present invention are described in PCT International Publication No. WO 89/06978 and European Patent Application No. 0 441 468 A2.

In particularly preferred embodiments, the liquid is substantially bubble-free at room temperature (e.g., about 20° C.), and the liquid particles form microbubbles when the temperature of the liquid is raised to body temperature of the mammal, for example, about 37° C., upon inhalation of the liquid particles by the mammal. This embodiment utilizes a liquid-gas phase change wherein the liquid aerosol particles remain a liquid or gas saturated liquid solution that cross the pulmonary alveolar membrane into the puliminary bloodstream, and thereafter release a sufficient volume of microbubbles due to an increase in temperature of the liquid particles to body temperature upon entering the bloodstream.

Alternatively, liquid aerosol particles can produce microbubbles upon entering a mammal's bloodstream by chemically reacting with components of the bloodstream.

In preferred embodiments in which the aerosol particles are liquid, the liquid can be a viscous solution, for example, by inclusion of one or more viscosity enhancers such as sorbitol. The use of viscous liquids can reduce the rate at which the microbubbles dissolve into the bloodstream and dissipate. Liquid particles of the aerosol can further include one or more of the following types of components: isotonic electrolytes such as NaCl, hydrophobic carrier liquids such as soybean oil, surfactants such as Tween 20, water and permeation enhancers such as dimethyl sulfoxide (DMSO) or 1-dodecylcylazacycloheptan-2-one (Azone) and/or ethanol.

In alternative embodiments, the particles of the aerosol are solid. Such solid particles can contain microbubbles and thus themselves comprise the ultrasonic image-enhancing microbubbles which form in the mammal's bloodstream. Alternatively, the solid particles can produce microbubbles upon entering the bloodstream by chemically reacting with components of the bloodstream. For example, a solid containing hydrogen peroxide within its structure such as inorganic phosphates, carbonates, and the like, or organic compounds such as urea, and the like, can be used.

In embodiments in which the contrast agent forms ultrasound image-enhancing microbubbles in the bloodstream, an imaging scan is performed by subjecting at least a portion of the mammal containing the microbubbles to an ultrasound scan, so as to obtain an enhanced ultrasonically generated image of that portion of the mammal.

In accordance with certain aspects of the present invention, aerosols of MRI contrast agents, such as suitable metal chelates, are provided. The metal chelates of the aerosol may include metals selected from the group consisting of lanthanide series members of atomic number 57–70, and transition metal members having an atomic number selected from the group consisting of 21–29, 42 and 44.

Generally, such MRI contrast agents will further include a pharmaceutically acceptable carrier.

Examples of paramagnetic metal chelate MRI contrast agents include Gd $(DTPA)^{2-}$:gadolinium (III)-diethylenetriamine-N,N,N',N",N"-pentaacetate; Gd(DTPA)-BMA:gadolinium(III)-diethylenetriamine-N,N,N',N",N"-pentaacetate-bis(methylamide); Dy(DTPA)$^{2-}$:Dysprosium(III)-diethylenetriamine-N,N,N',N",N"-pentaacetate; GD(DOTA)$^{-}$: gadolinium(III)-1,4,7,10-tetraazacyclododecane-N,N',N",N"-tetraacetate; Mn(CDTA)$^{2-}$: manganese(II)-trans--1,2-cyclohexylenedinitrilotetraacetate; Mn(NOTA)$^{-}$-:manganese(II)-1,4,7-triazacyclonoane-N,N',N"-triacetate; MN(EDTA)$^{2-}$:manganese(II)-ethylenediaminetetracetate; Mn(HEDTA)$^{-}$:managnese(II)-hydroxylethylethylenediaminetriacetate; Fe(EHPG):Iron(III)-N,N'-ethylenebis(2-hydroxyphenylglycine)ethylenediamine; FE(HBED):Iron(III)-N,N'-bis(2-hyroxybenzyl-)ethylenediaminediacetate, and the like.

Preferred MRI agents are chelates of Gadolinium, Iron or Manganese.

Suitable MRI agents may also include nitroxide radicals, other stabilized radicals or oxygen gas. Stable organic free radicals include DOXYL:(4,4-dimethyl-3-oxazolidinyloxy, free radical); PROXYL:(2,2,5,5-tetramethylpyrrolidine-1-oxyl, free radical, as an example 2,2,5,5-tetramethylpyrrolidine-1-oxyl-3-carboxylic acid); TEMPO:(2,2,6,6-tetramethyl-1-piperidinyloxy, free radical, as an example 2,2,6,6-tetramethyl-1-piperidine-1-oxyl-4-carboxylic acid), and the like.

The particles of the aerosol can also comprise a solution or a suspension of highly fluorinated hydrocarbons for magnetic resonance imaging of $F^{19}$ nuclei. Such $F^{19}$ MRI contrast agents can include biocompatible formulations of perfluorocarbons, such as perfluorooctylbromide and the like.

Particles containing MRI contrast agent can further include a lung tissue permeation enhancing substance such as DMSO, Azone and/or ethanol. Such permeation enhancing substances facilitate delivery of sufficient concentrations of contrast agent into the pulmonary blood for enhanced imaging of organs such as the liver, spleen, heart, etc.

When the contrast agent of the invention is an optical contrast agent, it can provide either positive or negative optical contrast. An image scan is performed by subjecting at least a portion of said mammal containing said agent to an optical scan utilizing electromagnetic radiation, so as to obtain an enhanced optical image of said portion of said mammal. Optical contrast agents according to the invention may comprise suitable optical dyes, such as emr-absorbing and voltage-sensitive dyes which are safe for in vivo administration. Such dyes may be selected from the group consisting of cyanines, merocyanines, oxonols, styryl dyes, and the like. One such dye is merocyanine oxazolone. The particles may comprise a solution or a suspension of the optical contrast agent, and may further comprise a permeation enhancing substance, such as dimethyl sulfoxide, 1-dodecylcylazacycloheptan-2-one (Azone) and/or ethanol.

The invention is illustrated by the following examples, which are not intended to be limiting.

EXAMPLE 1

Chlorotrifluoromethane (Freon-11) was dissolved in dimethyl sulfoxide (DMSO) with Tween 20 surfactant. The solution thus formed remained a stable, clear liquid at room temperature in a capped vial. The solution produced a visible blush of very small bubbles when poured into either deionized 37° C. water or room temperature saline. This DMSO solution exhibited greater density than either the water or saline, and quickly dropped to the bottom of the vial containing the mixture. Even several minutes after combining with either the 37° C. water of the saline, subsequent mild agitation produced additional visible production of gas bubbles.

EXAMPLE 2

An ultrasound contrast agent as described in Example 1 is formed into an aerosol and inhaled by a patient so as to transmit the agent through the lungs of the patient into the patient's bloodstream, wherein the agent forms ultrasound image-enhancing microbubbles in the bloodstream. The patient then is subjected to an ultrasound scan, so as to obtain an enhanced ultrasonically generated image of the patient, primarily of the heart.

EXAMPLE 3

A 3% hydrogen peroxide solution was aspirated by a fluorocarbon propellant sprayer into an intestinal membrane. The membrane was placed in a normal saline solution at 37° C. containing about 1% heparinized canine blood. Microbubbles were noted forming on the outer surface of the membrane within less than a minute. Application of an aerosol of deionized water produced no discernible microbubbles.

EXAMPLE 4

An aerosol of 0.2% hydrogen peroxide as outlined in Example 3 is inhaled by a patient so as to transmit the agent through the lungs of the patient into the patient's bloodstream, wherein the agent forms ultrasound image-enhancing oxygen microbubbles in the bloodstream. The patient then is subjected to an ultrasound scan, so as to obtain an enhanced ultrasonically generated image of the patient, primarily of the heart.

EXAMPLE 5

An aerosol of N,N''-bis(N-(2-methoxyethyl)carbamoylmethyl) diethylenetriamine-N,N',N'-triacetatogadolinium(III) in dimethyl sulfoxide and water is inhaled by a patient so as to transmit the agent through the lungs of the patient into the patient's bloodstream, wherein the contrast enhancing agent is delivered into the bloodstream. The patient then is subjected to an magnetic resonance scan, so as to obtain an enhanced image of the particular area of interest of the patient.

EXAMPLE 6

An aerosol containing merocyanine oxazolone is inhaled by a patient so as to transmit the agent through the lungs of the patient into the patient's bloodstream, wherein the contrast enhancing agent is delivered into the bloodstream. The patient then is subjected to an optical scan, so as to obtain an enhanced image of the particular area of interest of the patient.

What is claimed is:

1. A method of imaging a non-lung portion of mammal; comprising:
   a) administering an aerosol contrast agent comprised of particles to a mammal by inhalation of said agent into a lung of said mammal, which agent is transmitted through said lung into the mammal's bloodstream for transport to a non-lung portion of said mammal to be imaged; and
   b) performing an imaging scan on a non-lung portion of said mammal containing said contrast agent, so as to obtain an enhanced image of said non-lung internal portion of said mammal.

2. The method of claim 1 wherein said particles are selected from the group consisting of liquid particles and solid particles.

3. The method of claim 2 wherein said agent forms ultrasound image-enhancing microbubbles in said bloodstream, and wherein said imaging scan is performed by subjecting at least a portion of said mammal containing said microbubbles to an ultrasound scan, so as to obtain an enhanced ultrasonically generated image of said portion of said mammal.

4. The method of claim 3 wherein said agent further comprises a permeation enhancing substance.

5. The method of claim 4 wherein said permeation enhancing substance is selected from the group consisting of dimethyl sulfoxide, 1-dodecylcylazacycloheptan-2-one (Azone) and ethanol.

6. The method of claim 3 wherein said particles release microbubbles upon entering said bloodstream.

7. The method of claim 6 wherein said particles of said aerosol are liquid.

8. The method of claim 7 wherein said microbubbles comprise at least one member selected from the group consisting of hydrocarbons, fluorocarbons, fluorohalocarbons, ethers and mixtures thereof.

9. The method of claim 7 in which said liquid is substantially bubble-free at a temperature of about 20° C., wherein said liquid forms microbubbles when the temperature of said liquid is raised to about 37° C.

10. The method of claim 9 wherein said microbubbles comprise at least one member selected from the group consisting of fluorocarbon gases, fluorohalocarbon gases, hydrocarbon gases, volatile ethers and mixtures thereof.

11. The method of claim 6 wherein said particles of said aerosol are liquid containing at least one gas.

12. The method of claim 11 wherein said microbubbles comprise at least one gaseous propellant.

13. The method of claim 2 wherein said agent is a magnetic resonance contrast agent, wherein said agent provides either positive or negative image contrast, and wherein said image scan is performed by subjecting at least a portion of said mammal containing said agent to a magnetic resonance scan, so as to obtain an enhanced magnetic resonance image of said portion of said mammal.

14. The method of claim 13 wherein said particles of said aerosol comprise metal chelates.

15. The method of claim 14 wherein said metal chelates of said aerosol are selected from the group consisting of lanthanide series members of atomic numbers 57–70, and transition metal members having an atomic number selected from the group consisting of 21–29, 42 and 44; said agent further comprising a pharmaceutically acceptable carrier.

16. The method of claim 14 wherein said metal chelates of said particles are selected from the group consisting of gadolinium chelates, iron chelates, and manganese chelates.

17. The method of claim 13 wherein said particles in said aerosol comprise nitroxide radicals.

18. The method of claim 17 wherein said particles comprise a solution or a suspension of said highly fluorinated hydrocarbons said particles further comprising a permeation enhancing substance.

19. The method of claim 18 wherein said permeation enhancing substance is selected from the group consisting of dimethyl sulfoxide, 1-dodecytcylazacycloheptan-2-one (Azone) and ethanol.

20. The method of claim 13 wherein said particles of said aerosol comprise highly fluorinated hydrocarbons for magnetic resonance imaging of $F^{19}$ nuclei.

21. The method of claim 2 wherein said agent comprises an optical contrast agent, wherein said optical contrast agent provides either positive or negative optical contrast, and wherein said image scan is performed by subjecting at least a portion of said mammal containing said agent to an optical scan, so as to obtain an enhanced optical image of said portion of said mammal.

22. The method of claim 21 wherein said agent is an optical dye.

23. The method of claim 21 wherein said particles comprise a solution or a suspension of said optical contrast agent, said particles further comprising a permeation enhancing substance.

24. The method of claim 23 wherein said permeation enhancing substance is selected from the group consisting of dimethyl sulfoxide, 1-dodecylcylazacycloheptan-2-one (Azone) and ethanol.

25. A contrast agent for imaging a non-lung portion of a mammal, which comprises an aerosol including particles which are capable of entering a mammal's bloodstream through inhalation of said aerosol into a lung of the mammal, wherein said particles, upon introduction into the bloodstream of said mammal after inhalation by said mammal, form a contrast medium in said bloodstream, which contrast medium is transported to a non-lung portion of said mammal and is capable of enhancing images of said non-lung portion of said mammal.

26. The contrast agent of claim 25 wherein said particles are selected from the group consisting of liquid and solid particles.

27. The contrast agent of claim 26 wherein said particles form a contrast medium comprising microbubbles upon introduction into said bloodstream, which microbubbles are capable of enhancing an ultrasonically generated image of said non-lung portion of said mammal.

28. The contrast agent of claim 27 wherein said particles of said aerosol are solid, and wherein said particles comprise said microbubbles upon introduction into said bloodstream.

29. The contrast agent of claim 27 wherein said particles release microbubbles upon entering said bloodstream.

30. The contrast agent of claim 27 wherein said particles of said aerosol are liquid.

31. The contrast agent of claim 30 wherein said microbubbles comprise at least one gaseous propellant.

32. The contrast agent of claim 30 in which said liquid is substantially bubble-free at a temperature of about 20° C., wherein said liquid forms microbubbles when the temperature of said liquid is raised to about 37° C.

33. The ultrasound contrast agent of claim 30 wherein said microbubbles comprise at least one member selected from the group consisting of fluorocarbon gases, fluorohalocarbon gases, hydrocarbon gases, volatile ethers and mixtures thereof.

34. The contrast agent of claim 30 wherein said particles further comprise at least one member selected from the group consisting of hydrocarbons, fluorocarbons, and fluorohalocarbons.

35. The contrast agent of claim 30 wherein said particles further comprise at least one propellant gas.

36. The contrast agent of claim 30 wherein said particles are saturated with carbon dioxide.

37. The contrast agent of claim 25 wherein said particles further comprise a permeation enhancing substance.

38. The contrast agent of claim 37 wherein said permeation enhancing substance is selected from the group consisting of dimethyl sulfoxide, 1-dodecylcylazacycloheptan-2-one (Azone) and ethanol.

* * * * *

UNITED STATES PATENT AND TRADEMARK OFFICE
CERTIFICATE OF CORRECTION

PATENT NO. : 5,406,950
DATED : April 18, 1995
INVENTOR(S) : Gary H. Brandenburger et al.

It is certified that error appears in the above-indentified patent and that said Letters Patent is hereby corrected as shown below:

In the Claims:

Col. 7, lines 54-55 (claim 19), "1-dodecytcylazacycloheptan-2-one" should read --1-dodecylcylazacycloheptan-2-one--

Signed and Sealed this

Twenty-seventh Day of June, 1995

Attest:

BRUCE LEHMAN

Attesting Officer          Commissioner of Patents and Trademarks